Figure 1:
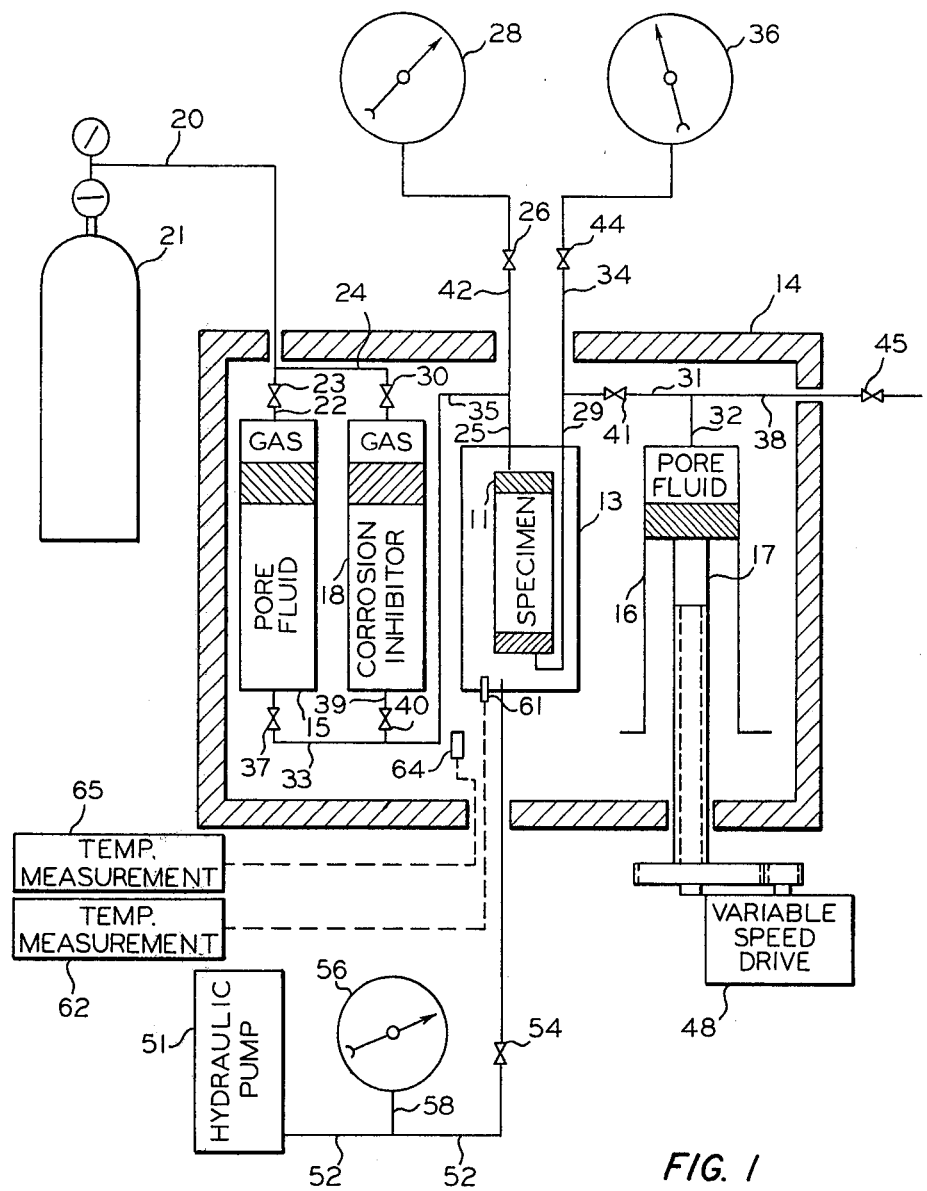

United States Patent [19]

Wiley

[11] 4,253,327
[45] Mar. 3, 1981

[54] METHOD AND APPARATUS FOR MEASURING ROCK PERMEABILITY AT ELEVATED PRESSURES AND TEMPERATURE

[75] Inventor: Bruce F. Wiley, Bartlesville, Okla.

[73] Assignee: Phillips Petroleum Company, Bartlesville, Okla.

[21] Appl. No.: 75,880

[22] Filed: Sep. 17, 1979

[51] Int. Cl.³ .......................................... G01N 15/08
[52] U.S. Cl. ..................................................... 73/38
[58] Field of Search ............................................ 73/38

[56] References Cited

U.S. PATENT DOCUMENTS

| | | | |
|---|---|---|---|
| 2,345,935 | 4/1944 | Hassler | 73/38 |
| 2,437,935 | 3/1948 | Brunner et al. | 73/38 |
| 2,521,079 | 9/1950 | Morris | 73/38 |
| 2,705,418 | 4/1955 | Reichertz et al. | 73/38 |
| 2,737,804 | 3/1956 | Herzog et al. | 73/38 |
| 3,199,341 | 8/1965 | Heuer, Jr. et al. | 73/38 X |
| 3,405,555 | 10/1968 | Wissinger et al. | 73/159 |
| 3,420,093 | 1/1969 | Collins | 73/38 |

OTHER PUBLICATIONS

Newman, G. H. et al., *Equipment & Experimental Methods for Obtaining Laboratory Compression Characteristics of Reservoir Rocks Under Various Stress & Pressure Conditions*, SPE6855, Oct. 1977, pp. 1-16.

*Primary Examiner*—Gerald Goldberg
*Assistant Examiner*—Joseph W. Roskos

[57] ABSTRACT

The permeability of a rock formation is determined at elevated pressures and temperature by heating a core sample taken from the rock formation and a fluid which is utilized to determine the permeability of the core sample to an elevated temperature. The fluid is injected under pressure and a second pressure which is higher than the injection pressure is applied to the surface area of the core sample. The effect of injecting a fluid such as a corrosion inhibitor or a polymer useful in secondary or tertiary recovery techniques on the permeability of the rock formation can be determined at elevated pressures and temperature by comparing the permeability of the rock formation before the fluid is injected and after the fluid is injected.

19 Claims, 2 Drawing Figures

METHOD AND APPARATUS FOR MEASURING ROCK PERMEABILITY AT ELEVATED PRESSURES AND TEMPERATURE

This invention relates to method and apparatus for ascertaining the permeability of a rock formation. In one aspect this invention relates to method and apparatus for ascertaining the permeability of a rock formation at elevated pressures and temperature. In another aspect this invention relates to method and apparatus for determining the effect of injecting a fluid, such as a corrosion inhibitor or a polymer useful in secondary or tertiary recovery techniques into a rock formation, on the permeability of the rock formation at elevated pressures and temperature.

A knowledge of the permeability of a rock formation is an essential parameter for determining the ability of a fluid to circulate in the pores of the rock formation. A knowledge of the permeability of a rock formation is particularly critical in oil and gas production and is essential in exploring subterranean formations to locate fluids such as oil or gas, in drilling wells into rock formations and in treating rock formations to improve production of fluids contained in the rock formation. It is particularly important, in treating rock formations, to improve production, to avoid some adverse effect such as corrosion, and to have a knowledge of the effect of the treating substance on the porosity of the rock formation. Injection of a substance which has an adverse effect on the permeability of a rock formation can have a disasterous effect on production.

In general, the permeability of a rock formation is determined by obtaining sample cores from the rock formation. The sample cores are then subjected to tests under standardized conditions to obtain a permeability value. Permeability is normally measured in millidarcys or darcys. A darcy may be defined as the rate of flow in millimeters per second of a fluid, having an adjusted viscosity of 1 centipoise, through a cross-section of one square centimeter specimen of material, under a pressure gradient of one atmosphere per centimeter of length of the specimen. The known formula for determining permeability, which was developed by Henry Darcy, may be expressed as follows:

$$K = Q\mu L / A \Delta P \quad (I)$$

where
- K = permeability in darcys,
- Q = flow rate in millimeters per second,
- A = cross-sectional area of core in cm$^2$,
- $\Delta P$ = pressure gradient in atmospheres,
- L = length of core in centimeters, and
- $\mu$ = viscosity of fluid employed in tests.

The permeability of a rock formation is generally measured by forcing fluid to flow at a known flow rate through a core sample. The pressure drop across the core sample is then measured and this pressure drop together with the viscosity of the fluid, length of the core, cross-sectional area of the core and viscosity of the fluid flowing through the core, all of which may be measured, are substituted into equation (I) to obtain the permeability of the rock formation. The effect of an injected substance on the permeability of a rock formation is typically measured by comparing the permeability of the core sample before and after the substance is injected.

In the past, it has been common to measure permeability of a core sample or measure the effect of an injected substance on the permeability of a core sample under standard conditions such as atmospheric pressure and room temperature. Measurements of the permeability of a rock formation under standard conditions such as atmospheric pressure and room temperature fail to consider the effect of pore pressure, overburden pressure, and temperature of the formation from which the core specimen was derived. The pore size may change and microscopic cracks will generally occur in a core sample when the sample is removed from the rock formation because of the change in pore pressure, overburden pressure and temperature to which the core sample is subjected. These changes will generally affect the permeability of the core sample. Therefore, if the in situ permeability of the core specimen or the in situ effect of an injected substance on the permeability of the core sample is desired, then in situ environmental conditions must be included in the permeability measurement or an error may be present in the measured permeability or measured effect of an injected substance on the permeability of the core sample.

It is thus an object of this invention to provide method and apparatus for ascertaining the permeaility of a rock formation at elevated temperature and pressures. It is another object of this invention to provide method and apparatus for determining the effect, of injecting a fluid such as a corrosion inhibitor or a polymer useful in secondary or tertiary recovery techniques into a rock formation, on the permeability of the rock formation at elevated pressures and temperature. Measurement of the permeability of a rock formation at elevated temperature and pressures, which may simulate reservoir conditions, provides a more accurate measurement of the permeability of the rock formation and thus provides more accurate data on which exploration for and production of fluids contained in a rock formation can be based.

In accordance with the present invention, method and apparatus is provided for forcing a fluid, which is preferably the fluid produced from the rock formation, through a core sample at a pressure which preferably represents the pore pressure in the reservoir or the reservoir driving force. A pressure, which preferably represents the overburden loading pressure, is provided around the outside of the core spceimen. The entire apparatus containing the core specimen and the fluid which is to be forced through the core specimen is contained in an oven which is utilized to heat both the core specimen and the fluid and the apparatus associated with the core specimen and the fluid to a temperature which preferably simulates the temperature of the rock formation from which the core sample was taken.

Initially, the oven and its contents are brought to the desired temperature and the pressures are adjusted to desired levels. Once the temperature and pressures have been stabilized, the flow of fluid through the core specimen is initiated and is maintained at a constant rate. The pressure differential across the core specimen, at a constant flow rate, is measured and this measurement coupled with a knowledge of the fluid viscosity and measurements of the core sample allow permeability to be calculated utilizing equation (I).

If the effect of injecting a fluid such as a corrosion inhibitor or polymer is to be studied, the permeability of the core sample is determined as has been previously described. The flow of the injected fluid through the core sample is then initiated. The core sample is then flushed with the original fluid (preferably the pore fluid) and the permeability of the core sample is again measured as has been previously described. A comparison of the permeability of the core sample before and after the injected fluid is allowed to flow through the core sample provides a measurement of the effect of the injected fluid on the permeability of the core sample at elevated temperature and pressures which preferably simulate reservoir conditions.

Figure 2:
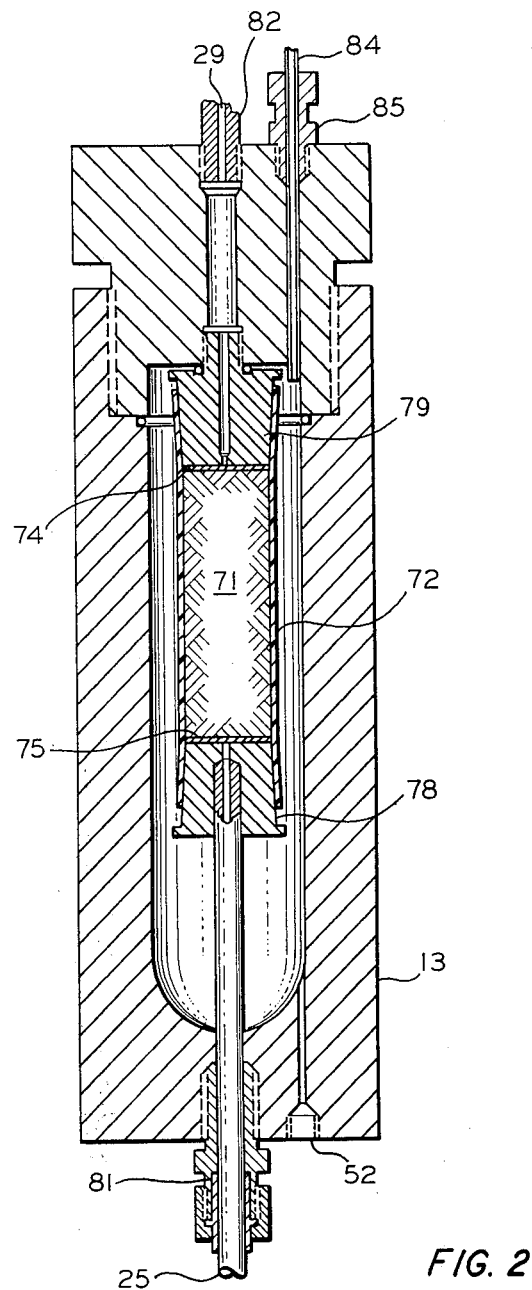

Other objects and advantages of the invention will be apparent from the forgoing brief description of the invention and the claims as well as from the detailed description of the drawings in which:

FIG. 1 is a diagrammatic view of the apparatus of the present invention for measuring the permeability of a core sample under reservoir conditions; and FIG. 2 is a more detailed diagrammatic illustration of the apparatus utilized to hold the core sample and force fluid through the core sample.

The invention is described in terms of a particular apparatus and in terms of particular method steps. However, the invention is not limited to the particular apparatus utilized to describe the invention and is not limited to the particular method steps which are presently preferred. The invention is applicable to any apparatus and any set of method steps which accomplish the purpose of the present invention.

The invention is also described in terms of measuring the permeability of the core sample at pressures and temperature which simulate reservoir conditions. However, the invention is applicable to measuring the permeability of the core sample at any elevated temperature and pressures. Further, the invention is described in terms of using the pore fluid obtained from the rock formation to measure the permeability of the core sample. However, any suitable fluid could be utilized to measure the permeability of the core sample. Further, the invention is described in terms of determining the effect of a corrosion inhibitor on the permeability of the core sample. However, the invention is applicable to determining the effect of any injected fluid on the permeability of the core sample.

Referring now to the drawings, and in particular to FIG. 1, a jacketed core specimen 11 is confined within the hydrostatic cell 13. The hydrostatic cell 13 is located in the oven 14. A free piston accumulator 15 which contains the pore fluid and a free piston accumulator 18 which contains the corrosion inhibitor as well as the cylinder 16 which is equipped with a power-driven piston 17 are also contained in the oven 14. The free piston in the free piston accumulator 15 separates pore fluid, which is preferably obtained from the reservoir from which the jacketed core specimen 11 was taken, from an inert gas such as nitrogen. The free piston in the free piston accumulator 18 separates corrosion inhibitor from the inert gas such as nitrogen. The inert gas is provided from the gas cylinder 21 to the free piston cylinder 15 through the combination of conduit means 20 and 22. Control valve 23 is operably located in conduit means 22. The inert gas is provided from the gas cylinder 21 through combination of conduit means 20 and 24 to the free piston cylinder 18. The control valve 30 is operably located in conduit means 24. Pore fluid is provided from the free piston cylinder 15 through the combination of conduit means 33, conduit means 35 and conduit means 25. Control valve means 37 is operably located in conduit means 33. Corrosion inhibitor is provided from the free piston cylinder 18 through the combination of conduit means 39, conduit means 35 and conduit means 25 to the jacketed core specimen 11. Control valve 40 is operably located in conduit means 39. Either pore fluid or corrosion inhibitor may be provided through conduit means 42 in which control valve 26 is operably located to the pressure gauge 28.

Either pore fluid or a combination of pore fluid and corrosion inhibitor flows through the jacketed core specimen 11 and is provided through the combination of conduit means 29, 31 and 32 to the cylinder 16. Fluid is also provided from the jacketed core specimen 11 through the combination of conduit means 29 and 34 to the pressure gauge 36. The fluid flowing from the jacketed core specimen 11 may also be exhausted from the oven 14 through the combination of conduit means 29, 31 and 38. The control valve 41 is operably located in conduit means 31; the control valve 44 is operably located in conduit means 34; and the control valve 45 is operably located in conduit means 38.

Power is provided to move the piston 17 by the variable speed drive motor 48. The variable speed drive motor 48 is preferably a synchronous motor having a gear change mechanism which can furnish a constant flow rate ranging in steps from 1 to about 1,000 milliliters per hour. A motor such as the Model 714628-QC, Type-PR, FR-R56C 3$\phi$ 60H3 manufactured by Reliance Electric Co., Euclid Avenue, Cleveland, Ohio 4418 may be utilized if desired.

Overburden pressure is applied to the jacketed specimen 11 by means of the hydraulic pump 51 which pumps fluid through the combination of conduit means 52 and 53 to the hydrostatic cell 13 which is preferably filled with hydraulic oil. Control valve means 54 is operably located in conduit means 52. The hydraulic pump 51 also provides fluid to the pressure gauge 56 through the combination of conduit means 52 and 58. Any suitable hydraulic pump may be utilized. A Model CP04-160 pump manufactured by Star Hydraulics, Inc., 2727 Clinton St., River Grove, Illinois is presently preferred.

A temperature measuring device, such as the thermocouple 61, provides an indication of the temperature in the hydrostatic cell 13 to the temperature measuring device 62 which may be a digital thermometer. In like manner, the thermocouple 64 provides a signal representative of the temperature in the oven 14 to the temperature measuring device 65 which also may be a digital thermometer.

A typical sequence for measuring the permeability of a core sample using the apparatus illustrated in FIG. 1 is as follows. A core specimen from a rock formation is first prepared and placed in the hydrostatic cell 13. The hydrostatic cell 13 is then filled with hydraulic oil. The lower portion of the free piston accumulator 15 is filled with a pore fluid such as oil and again this pore fluid is preferably the pore fluid which would be found in the rock formation from which the core specimen was taken. Control valves 23, 26, 44 and 37 are opened and the pressure supplied from the gas cylinder 21 is manipulated until the pressure gauge 28 indicates that a desired pore pressure, which simulates that found in the rock formation from which the core specimen was taken, has been obtained. An overburden pressure, which will typically be greater than the pore pressure, is supplied from the hydraulic pump 51. The oven temperature is then increased to a desired temperature and the pressures are adjusted to compensate for expanding fluids. Once temperatures and pressures have been stabilized, the flow of pore fluid through the core specimen 11 is initiated and maintained by starting the variable speed drive motor 48 which withdraws the piston 17 in the cylinder 16 thus allowing fluid to flow through the core specimen 11 at a desired constant rate. After the differential pressure across the core sample 11 becomes constant at the constant flow rate of pore fluid through the core sample, the pressure differential between the pressure gauge 28 and pressure gauge 36 is noted. The permeability of the core specimen may then be calculated utilizing equation (I) based on the measured pressure differential, the viscosity of the pore fluid, the known flow rate of the pore fluid through the core specimen and the physical measurements of the core specimen.

A typical sequence for measuring the effect of the corrosion inhibitor on the permeability of the core sample using the apparatus illustrated in FIG. 1 is as follows. The permeability of the core sample is first measured as has been previously described. Control valve 37 is closed and control valves 30 and 40 are opened. Corrosion inhibitor is allowed to flow through the core specimen for a desired length of time usually sufficient to displace existing pore fluids in the jacketed core specimen 11. The flow of the corrosion inhibitor is then cut off by closing control valves 30 and 40 and the corrosion inhibitor is flushed from the jacketed core specimen 11. The permeability of the core sample is then measured as has been previously described. A comparison of the measurement of the permeability of the core specimen prior to introduction of the corrosion inhibitor and after introduction of the corrosion inhibitor provides a measurement of the effect of the corrosion inhibitor on the core sample.

The hydrostatic cell 13 which contains the jacketed core specimen 11 is more fully illustrated in FIG. 2. Referring now to FIG. 2, the core specimen 71 is preferably surrounded by a thin, Teflon sleeve 72 which preferably has an inside diameter of 1". The Teflon sleeve 72 preferably extends 1" past both ends of the core sample 71. Sintered metal plates 74 and 75, which are preferably made from stainless steel, are placed against each end of the core sample 71. End plugs 78 and 79 are utilized to hold the core sample 71 and the sintered metal plates 74 and 75 in place. Conduit means 25 extends through the packing gland 81 to the sintered metal plate 75. Conduit means 29 extends through the pressure fitting 82 to the sintered metal plate 74. The thermocouple 61 illustrated in FIG. 1 is inserted into the thermocouple well 84 which is operably connected to the hydrostatic cell 13 by means of the pressure fitting 85. Conduit means 52 extends into the hydrostatic cell 13 as is illustrated in FIG. 2.

In operation, fluid flow through conduit means 25 and the sintered metal plate 75 into the core specimen 71. After passing through the core specimen 71, the fluid flows out of the sintered metal plate 74 and through the conduit means 29. Overburden pressure is provided to the core specimen 71 by means of pressure applied through conduit means 52 as has been previously stated.

The following example is presented in further illustration of the invention.

EXAMPLE

Core samples, 1" in diameter and ranging from 1½ to 2" in length were drilled from cores taken from an oil-bearing rock formation. The core samples were cleaned in a Soxhlet extractor using methyl alcohol, toluene and tetrahydrofuran as alternating solvents until the effluents were clear of tinting. The porosity and specific permeability to nitrogen gas and grain density measurements were made on each sample. Dry weights were determined and the samples were then evacuated for about 16 hours before they were saturated with filtered (0.45 microns) formation water. To assure complete saturation, the samples were placed into a pressure cell under formation water and pressured to 2500 psi (1723.75 kPa) for about 16 hours. After removal from the pressure cell, the core samples were then weighed and the water volume in place was compared to the pore volume of each sample to check for complete water saturation. Each water-saturated core sample was then placed into the Teflon sleeve 72 illustrated in FIG. 2. The sintered metal plates 74 and 75, which were water-saturated, were then inserted into the Teflon sleeve and placed flatly next to each end of the core sample 71. The end plugs 79 and 78 were then inserted into the teflon sleeve. The hydrostatic cell 13 was then filled with hydraulic oil. The hydrostatic cell 13 was then secured in the oven 14 and the necessary conduits were connected to the hydrostatic cell 13. The pressure on the pore fluid in the free piston accumulator 15 was then increased until the pressure gauge 28 registered a pressure of 6200 psi (4274.9 kPa). Overburden pressure was applied to the jacketed core specimen until the pressure gauge 56 measured 7200 psi (4964.4 kPa). This provided a net combined pressure of 1,000 psi (6895 kPa) on the core sample. The temperature of the oven 14 was then increased to 265° F. (129.44° C.) and this temperature was maintained for about 4 hours to allow the temperature to become constant throughout the system contained in the oven 14. Formation crude oil was then flushed through the water-saturated core sample at a high rate of flow displacing the water to bring the water content to an irreducible level. The flow rate of the formation crude oil was then dropped to 200 milliliters per hour which is equivalent to a standard production rate. After the differential pressures, as measured by the pressure gauges 28 and 36, became constant at the 200 milliliter/hour flow rate, the pressure differential was noted and the flow of formation crude oil was halted. This pressure differential was utilized to calculate the permeability of the core specimen utilizing equation (I).

Corrosion inhibitors combined with diesel fuel oil were then injected into the core sample. The pore system of the hydrostatic cell was then shut-in for about 24 hours. After the 24 hour corrosion inhibitor exposure time, the core plug samples were flushed with the formation crude oil at the flow rate of 200 milliliters per hour. After the differential pressure, as measured by the pressure gauges 28 and 36, became constant, the differential pressure was again noted and the permeability of the core sample was again calculated based utilizing equation (I).

Results of the test are set forth in Table I.

TABLE I

EFFECT OF CORROSION INHIBITORS ON EFFECTIVE PEREABILITY OF CORE SAMPLES

| Core Speciman | Percent Porosity | Nitrogen Permeability, md | Initial Permeability to Oil, md | Final Permeability to Oil After Exposure to Corrosion Inhibitor | Corrosion Inhibitor |
|---|---|---|---|---|---|
| 1 | 40.5 | 5.80 | 1.05 | 1.02 | 1 |
| 2 | 42.4 | 7.01 | 1.56 | 1.31 | 1 |
| 3 | 41.3 | 6.86 | 1.32 | 1.57 | 1 |
| 4 | 40.8 | 6.65 | 1.22 | 1.14 | 1 |
| 5 | 41.7 | 7.01 | 2.07 | 0.74 | 2 |
| 6 | 43.4 | 9.37 | 1.74 | 0.62 | 2 |
| 7 | 42.0 | 5.17 | 0.72 | 0.62 | 3 |
| 8 | 45.6 | 7.85 | 1.94 | 1.48 | 3 |
| 9 | 39.6 | 5.26 | 0.92 | 0.50 | 4 |
| 10 | 38.4 | 4.43 | 0.86 | 0.34 | 4 |
| 11 | 37.6 | 3.96 | 0.66 | 0.43 | 5 |
| 12 | 37.4 | 3.42 | 0.52 | 0.58 | 6 |
| 13 | 37.7 | 6.11 | 1.25 | 0.97 | 6 |
| 14 | 38.7 | 5.12 | 0.77 | 0.78 | 7 |
| 15 | 38.6 | 5.251 | 0.76 | 0.78 | 8 |

Note:
md = millidarcys

It is first noted that the method and apparatus of the present invention could be utilized simply to measure the permeability of a core specimen under reservoir conditions. The method and apparatus of the present invention also can be utilized to determine the effect of a substance such as a corrosion inhibitor on a rock formation by determining the effect of the corrosion inhibitor on a core sample taken from the rock formation. As is illustrated in Table I, some corrosion inhibitors cause severe plugging of the core sample and thus would be undersirable for injection into the rock formation.

Reasonable variations and modifications are possible within the scope of the disclosure and the appended claims to the invention.

That which is claimed is:

1. A method for determining the permeability of a core sample, having first and second faces, at an elevated temperature and elevated pressures comprising the steps of:
   heating said core sample and a fluid to a desired temperature;
   supplying said fluid under a first desired pressure to the first face of said core sample;
   enabling said fluid to flow through said core sample at a desired, substantially constant flow rate;
   applying a second desired pressure to the surface area of said core sample, said second desired pressure being greater than said first desired pressure;
   measuring the pressure of the fluid flowing to the first face of said core sample;
   measuring the pressure of the fluid flowing from the second face of said core sample;
   comparing the measured pressure of the fluid flowing to the first face of said core sample to the measured pressure of the fluid flowing from the second face of said core sample to determine the pressure differential across said core sample; and
   calculating the permeability of said core sample based on the pressure differential across said core sample.

2. A method in accordance with claim 1 wherein said step of calculating the permeability of said core sample based on the pressure differential across said core sample comprises:
   multiplying said substantially constant flow rate (Q) by the viscosity ($\mu$) of said fluid to establish the term $Q\mu$;
   multiplying the term $Q\mu$ by the length (L) of said core sample to establish the term $Q\mu L$;
   multiplying said pressure differential ($\Delta P$) by the crosssectional area (A) of said core sample to establish the term $A\Delta P$; and
   dividing the term $Q\mu L$ by the term $A\Delta P$ to thereby establish the permeability of said core sample.

3. A method in accordance with claim 1 wherein said core sample is a cylindrical body and said first and second faces are first and second ends of the cylindrical body.

4. A method in accordance with claim 1 wherein said desired temperature is a temperature which corresponds to the temperature of the rock formation from which said core sample was taken, said first desired pressure is the pore pressure in the rock formation from which said core sample was taken, said second desired pressure is the overburden pressure on the rock formation from which the core sample was taken, and said fluid is the pore fluid from the rock formation from which the core sample was taken.

5. A method in accordance with claim 1 wherein said step of applying a second desired pressure to the surface area of said core sample comprises:
   surrounding said core sample with hydraulic oil; and
   applying said second desired pressure to said hydraulic oil to thereby apply said second desired pressure to said core sample.

6. A method for determining the affect of a first fluid on the permeability of a core sample, having first and second faces, at an elevated temperature and elevated pressures comprising the steps of:
   heating said core sample, said first fluid and a second fluid to a desired temperature;
   supplying said second fluid under a first desired pressure to a first face of said core sample;
   enabling said second fluid to flow through said core sample at a desired, substantially constant flow rate;
   applying a second desired pressure to the surface area of said core sample, said second desired pressure being greater than said first desired pressure;
   measuring the pressure of the fluid flowing to the first face of said core sample;
   measuring the pressure of the fluid flowing from the second face of said core sample;
   comparing the measured pressure of the fluid flowing to the first face of said core sample to the measured pressure of the fluid flowing from the second face of said core sample to determine the pressure differential across said core sample before said first fluid is injected into said core sample;
   calculating the permeability of said core sample based on the pressure differential across said core sample before said first fluid is injected into said core sample;
   injecting said first fluid into said core sample;
   removing said first fluid by again enabling said second fluid to flow through said core sample at said desired, substantially constant flow rate;
   measuring the pressure of the fluid flowing to the first face of said core sample;
   measuring the pressure of the fluid flowing from the second face of said core sample;

comparing the measured pressure of the fluid flowing to the first face of said core sample to the measured pressure of the fluid flowing from the second face of said core sample to determine the pressure differential across said core sample after said first fluid has been injected into said core sample;

calculating the permeability of said core sample based on the pressure differential across said core sample after said first fluid has been injected into said core sample; and comparing the permeability of said core sample before said first fluid was injected into said core sample and after said first fluid was injected into said core sample to determine the effect of said first fluid on the permeability of said core sample.

7. A method in accordance with claim 6 wherein said step of calculating the permeability of said core sample based on the pressure differential across said core sample before said first fluid is injected into said core sample comprises:

multiplying said substantially constant flow rate (Q) by the viscosity ($\mu$) of said fluid to establish the term $Q\mu$;

multiplying the term $Q\mu$ by the length (L) of said core sample to establish the term $Q\mu L$;

multiplying the pressure differential ($\Delta P_1$) before said first fluid is injected into said core sample by the cross-sectional area (A) of said core sample to establish the term $A\Delta P_1$; and dividing the term $Q\mu L$ by the term $A\Delta P_1$ to thereby establish the permeability of said core sample before said first fluid is injected into said core sample.

8. A method in accordance with claim 7 wherein said step of calculating the permeability of said core sample based on the pressure differential across said core sample after said first fluid is injected into said core sample comprises:

multiplying said substantially constant flow rate (Q) by the viscosity ($\mu$) of said fluid to establish the term $Q\mu$;

multiplying the term $Q\mu$ by the length (L) of said core sample to establish the term $Q\mu L$;

multiplying the pressure differential ($\Delta P_2$) after said first fluid is injected into said core samle by the cross-sectional area (A) of said core sample to establish the term $A\Delta P_2$; and dividing the term $Q\mu L$ by the term $A\Delta P_2$ to thereby establish the permeability of said core sample after said first fluid is injected into said core sample.

9. A method in accordance with claim 6 wherein said core sample is a cylindrical body and said first and second faces are first and second ends of the cylindrical body.

10. A method in accordance with claim 6 wherein said desired temperature is a temperature which corresponds to the temperature of the rock formation from which said core sample was taken, said first desired pressure is the pore pressure in the rock formation from which said core sample was taken, said second desired pressure is the overburden pressure on the rock formation from which the core sample was taken, said second fluid is the pore fluid from the rock formation from which the core sample was taken, and said first fluid is a corrosion inhibitor.

11. A method in accordance with claim 6 wherein said step of applying a second desired pressure to the surface area of said core sample comprises:

surrounding said core sample with hydraulic oil; and applying said second desired pressure to said hydraulic oil to thereby apply said second desired pressure to said core sample.

12. Apparatus comprising:

a hydrostatic cell containing a core sample which has first and second faces;

means for supplying a first fluid under a first desired pressure to a first face of said core sample;

means for enabling said fluid to flow through said core sample at a desired, substantially constant rate;

means for maintaining said hydrostatic cell, said means for supplying said first fluid under a first desired pressure to a first face of said core sample, and said means for enabling said first fluid to flow through said core sample at a desired temperature;

means for applying a second desired pressure to the surface area of said core sample, said second desired pressure being greater than said first desired pressure;

means for measuring the pressure of the fluid flowing to the first face of said core sample; and means for measuring the pressure of the fluid flowing from the second face of said core sample, a comparison of the measured pressure of the fluid flowing to the first face of said core sample and the measured pressure of the fluid flowing from the second face of said core sample providing a determination of the pressure differential across said core sample, the pressure differential across said core sample being utilized to calculate the permeability of said core sample.

13. Apparatus in accordance with claim 12 wherein said means for supplying said first fluid under said first desired pressure to a first face of said core sample comprises:

a free piston accumulator containing said first fluid;

means for providing said first fluid from said free piston accumulator to the first face of said core sample in said hydrostatic cell; and means for applying pressure to the free piston in said free piston accumulator to thereby supply said first fluid under said first desired pressure to the first face of said core sample.

14. Apparatus in accordance with claim 13 wherein said means for enabling said first fluid to flow through said core sample comprises:

a cylinder having a piston operably located therein;

means for moving said piston at a desired rate;

means for supplying said first fluid from the second face of said core sample in said hydrostatic cell to the portion of said cylinder sealed by said piston, the movement of said piston in said cylinder controlling the flow of said first fluid through said core sample.

15. Apparatus in accordance with claim 14 wherein said means for applying said second desired pressure to the surface area of said core sample comprises:

means for filling said hydrostatic cell with hydraulic oil; and means for applying pressure to said hydraulic oil to thereby apply said second desired pressure to the surface area of said core sample.

16. Apparatus in accordance with claim 15 wherein said core sample is a cylindrical body and said first and secnd faces are first and second ends of said cylindrical body.

17. Apparatus in accordance with claim 16 wherein said first fluid is pore fluid found in the rock formation from which said core sample is taken, said first desired pressure is the pore pressure in said rock formation, said second desired pressure is the overburden pressure on said rock formation, and said desired temperature of said rock formation.

18. Apparatus in accordance with claim 12 additionally comprising:

means for injecting a second fluid into said core sample, the difference between the pressure differential across said core sample with said first fluid flowing through said core sample before said second fluid is injected into said core sample and after said second fluid is injected into said core sample providing an indication of the affect of said second fluid on the permeability of said core sample.

19. Apparatus in accordance with claim 18 wherein said second fluid is a corrosion inhibitor.

* * * * *